US006410028B1

(12) United States Patent
Srivastava

(10) Patent No.: US 6,410,028 B1
(45) Date of Patent: *Jun. 25, 2002

(54) THERAPEUTIC AND PROPHYLACTIC METHODS USING HEAT SHOCK PROTEINS

(75) Inventor: Pramod K. Srivastava, Riverdale, NY (US)

(73) Assignee: Fordham University, Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/372,022

(22) Filed: Aug. 9, 1999

Related U.S. Application Data

(62) Division of application No. 08/527,547, filed on Sep. 13, 1995, now Pat. No. 5,935,576.

(51) Int. Cl.[7] ..................... A61K 39/385; A61K 39/12; A61K 39/02; A61K 39/00; A61K 38/00
(52) U.S. Cl. ..................... 424/193.1; 424/194.1; 424/195.11; 424/196.11; 424/197.11; 424/277.1; 424/204.1; 424/234.1; 424/274.1; 514/12
(58) Field of Search ..................... 424/193.1, 277.1, 424/194.1, 195.11, 196.11, 197.11, 204.1, 234.1, 274.1; 514/12

(56) References Cited

U.S. PATENT DOCUMENTS

| 4,690,915 A | 9/1987 | Rosenberg |
| 5,188,964 A | 2/1993 | McGuire et al. |
| 5,232,833 A | 8/1993 | Sanders et al. |
| 5,348,945 A | 9/1994 | Berberian et al. |
| 5,750,119 A | 5/1998 | Srivastava |
| 5,830,464 A | 11/1998 | Srivastava |
| 5,837,251 A | 11/1998 | Srivastava |
| 5,935,576 A | 8/1999 | Srivastava |
| 5,961,979 A | 10/1999 | Srivastava |
| 5,985,270 A | 11/1999 | Srivastava |
| 5,997,873 A | 12/1999 | Srivastava |
| 6,017,544 A | 1/2000 | Srivastava |
| 6,030,618 A | 2/2000 | Srivastava |
| 6,048,530 A | 4/2000 | Srivastava |

FOREIGN PATENT DOCUMENTS

| DE | 19602 985 A1 | 1/1996 |
| GB | 2 251 186 A | 7/1992 |
| WO | WO 89/12455 | 12/1989 |
| WO | WO 90/02564 | 3/1990 |
| WO | WO 91/15572 | 10/1991 |
| WO | WO 92/01717 | 2/1992 |
| WO | WO 92/08484 | 5/1992 |
| WO | WO 92/08488 | 5/1992 |
| WO | WO 93/14118 | 7/1993 |
| WO | WO 93/17712 | 9/1993 |
| WO | WO 93/18146 | 9/1993 |
| WO | WO 93/18147 | 9/1993 |
| WO | WO 93/18150 | 9/1993 |
| WO | WO 93/21529 | 10/1993 |
| WO | WO 93/24136 | 12/1993 |
| WO | WO 94/03205 | 2/1994 |
| WO | WO 94/03208 | 2/1994 |
| WO | WO 94/04676 | 3/1994 |
| WO | WO 94/11513 | 5/1994 |
| WO | WO 94/29459 | 12/1994 |
| WO | WO 95/24923 | 9/1995 |
| WO | WO 96/10411 | 4/1996 |
| WO | WO 97/06685 | 2/1997 |
| WO | WO 97/06821 | 2/1997 |
| WO | WO 97/06828 | 2/1997 |
| WO | WO 97/26910 | 7/1997 |

OTHER PUBLICATIONS

U.S. patent application Ser. No. 08/462,395, Srivastava et al., filed Jun. 5, 1995.
Aldovini et al. (1992) "The New Vaccines", *Technology Review* pp. 24–31.
Barrios et al. (1992) "Mycobacterial heat–shock proteins as carrier molecules. II: The use of the 70–kDa mycobacterial heat–shock protein as carrier for conjugated vaccines that can circumvent the need for adjuvants and *Bacillus Calmette* Guérin priming", *Eur. J. Immunol.* 22:1365–1372.
Basombrio (1970) "Search for common antigenicities among twenty–five sarcomas induced by methylcholanthrene", *The Institute for Cancer Research* 30:2458–2462.
Blachere et al. (1993) "Heat Shock Protein Vaccines Against Cancer," *Journal of Immunotherapy* 14:352–356.
Blachere and Srivastava (1993) "Immunization with GP96 heat shock proteins isolated from tumors or influenza virus infected cells elicits HMC–restricted, antigen–specific cytotoxic T lymphocytes against the corresponding cells", *J. Cellular Biochem. Keystone Symposia* NZ502, p. 124.
Boon "Toward a genetic analysis of tumor rejection antigens", *Advances in Cancer Research* 58:177–210.
Cohen (1993) "Cancer Vaccines Get A Shot In The Arm", *Science* 262:841–843.
Craig (1993) "Chaperones: Helpers Along the Pathways to Protein Folding", *Science* 260:1902–1904.
Elliott et al. (1990) "Naturally Processed Peptides", *Nature* 348:195–197.
Falk et al. (1991) "Allele–specific Motifs Revealed by Sequencing of Self–peptides Eluted from MHC Molecules", *Nature* 351:290–296.
Falk et al. (1990) "Cellular Peptide Composition Governed by Major Histocompatibility Complex Class I Molecules", *Nature* 348:248–251.

(List continued on next page.)

Primary Examiner—Geetha P. Bansal
(74) *Attorney, Agent, or Firm*—Pennie & Edmonds LLP

(57) ABSTRACT

The present invention relates to immunogenic complexes of heat shock proteins (hsp) noncovalently bound to exogenous antigenic molecules which when administered to an individual elicit specific immunological responses in the host. Methods of prevention and treatment of cancer and infectious disease are provided.

15 Claims, 1 Drawing Sheet

OTHER PUBLICATIONS

Figure 1A:
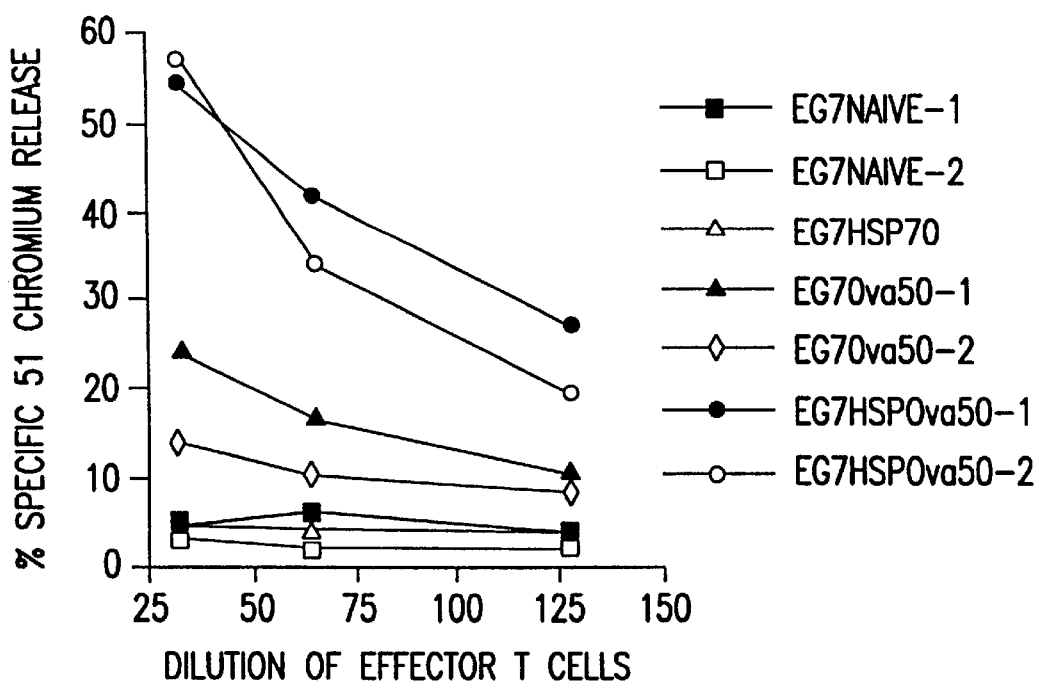

Fedweg and Srivastava "Evidence for biochemical heterogeneity of gp96 heat shock protein/tumor rejecion antigen", Mount Sinai School of Medicine NZ 206, p. 108.
Flynn et al. (1989) "Peptide binding and release by proteins implicated as catalysis of protein assembly", *Science* 245:385–390.
Flynn et al. (1991) "Peptide–binding Specificty of the Molecular Chaperone BiP", *Nature* 353:726–730.
Franklin (1993) "Making vaccines fit the cancer", *New Scientists* 140:17.
Gething et al. (1992) "Protein Folding in the Cell", *Nature* 355:33–45.
Globerson and Feldman (1964) "Antigenic specificity of benzo[a]pyrene–induced sarcomas", *Journal of the National Cancer Institute* 32(6):1229–1242.
Jakob et al. (1993) "Small Heat Shock Proteins Are Molecular Chaperones", *J. Biol. Chem.* 268:1517–1520.
Jardetzky et al. (1991) "Identification of Self Peptides Bound to Purified HLA–B27", *Nature* 353:326–329.
Lakey et al (1987) "Identification of a peptide binding protein that plays a role in antigen presentation", *Proc. Natl. Acad. Sci. USA* 84:1659–1663.
Lanzavecchia (1993) "Identifying Strategies for Immune Intervention", *Science* 260:937–944.
Lévy (1991) "ATP is Required for In Vitro Assembly of MHC Class I Antigens but Not for Transfer of Peptides across the ER Membrane", *Cell* 67:265–274.
Li and Srivastava (1993) "Tumor rejection antigen gp96/grp94 is an ATPase: Implications for protein folding and antigen presentation", *EMBO J.* 12(8):3143–3151.
Lindquist and Craig (1988) "The heat–shock proteins", *Ann. Rev. Genet.* 22:631–677.
Luescher et al. (1991) "Specific Binding of Antigenic Peptides to Cell–associated MHC Clas I Molecules", *Nature* 351:72–77.
Lukacs et al. (1993) "Tumor cells transfected with a bacterial heat–shock gene lose tumorigenicity and induce protection against tumors", *J. Exp. Med.* 178:343–348.
Lussow et al. (1991) "Mycobacterial heat–shock proteins as carrier molecules", *Eur. J. Immunol.* 21:2297–2302.
Madden et al. (1991) "The Structure of HLA–B27 Reveals Nonamer Self–peptides Bound in an Extended Conformation", *Nature* 353:321–325.
Maki et al. (1993) "Mapping of the Genes for Human Endoplasmic Reticular Heat Shock Protein gp96/grp94", *Somatic Cell Mol. Genetics* 19(1):73–81.
Maki et al. (1990) "Human homologue of murine tumor rejection antigen gp96: 5'–Regulatory and coding regions and relationship to stress–induced proteins", *Proc. Natl. Acad. Sci. USA* 87:5658–5663.
McCall et al. (1989) "Biotherapy: A New Dimension in Cancer Treatment", *Biotechnology* 7:231–240.
Melnick (1985) "Virus Vaccines: An Overview", Proceedings of the First Annual Southwest Foundation for Biomedical Research International Symposium, Houston, Texas, Nov. 8–10, 1984, *American Society for Microbiology* pp. 1–13.
Nelson et al. (1992) "The Translation Machinery and 70 kd Heat Shock Protein Cooperate in Protein Synthesis", *Cell* 71:97–105.
Palladino et al. (1987) "Expression of shared tumor–specific antigen by two chemically induced BALB/c sarcomas", *Cancer Research* 47:5074–5079.

Prehn and Main (1957) "Immunity to methylcholanthrene–induced sarcomas", *Journal of the National Cancer Institute* 18(6):769–778.
Rothman (1989) "Polypeptide Chain Binding Proteins: Catalysts of Protein Folding and Related Processes in Cells", *Cell* 59:591–601.
Rötzschke et al. (1990) "Isolation and Analysis of Naturally Processed Viral Peptides as Recognized by Cytotoxic T cells", *Nature* 348:248–251.
Salk et al. (1993) "A Strategy for Prophylactic Vaccination Against HIV", *Science* 260:1270–1272.
Schumacher et al. (1991) "Peptide Selection by MHC Class I Molecules", *Nature* 350:703–706.
Srivastava et al. (1991) "Protein Tumor Antigens", *Curr. Opin. Immunol.* 3:654–658.
Srivastava et al. (1984) "The Serologically Unique Cell Surface Antigen of Zajdela Ascitic Hepatoma is also its Tumor–Associated Transplantation Antigen", *Int. J. Cancer* 33:417–422.
Srivastava et al. (1989) "Identification of a Human Homologue of the Murine Tumor Rejection Antigen GP96," *Cancer Res.* 49:1341–1343.
Srivastava et al. (1988) "Individually Distinct Transplantation Antigens of Chemically Induced Mouse", *Immunology Today* 9:78–83.
Srivastava et al. (1988) "Chromosomal Assignment of the Gene Encoding the Mouse Tumor Rejection Antigen gp96", *Immunogenetics* 28:205–207.
Srivastava et al. (1987) "5'–Structural analysis of genes encoding polymorphic antigens of chemically induced tumors", *Proc. Natl. Acad. Sci. USA* 84:3807–3811.
Srivastava et al. (1993) "Peptide–Binding Heat Shock Proteins in the Endoplasmic Reticulum: Role in Immune Response to Cancer and in Antigen Presentation", *Advances in Cancer Research* 62:153–177.
Srivastava and Maki (1991) "Stress–induced proteins in immune response cancer", *Curr. Topic Microbiol. Immunol.* 167:109–123.
Srivastava and Heike (1991) "Tumor–specific immunogenicity of stress–induced proteins: Convergence of two evolutionary pathways of antigen presentation?", *Seminars in Immunology* 3:57–64.
Srivastava et al. (1986) "Tumor rejection antigens of chemically induced sarcomas of inbred mice", *Proc. Natl. Acad. Sci. USA* 83:3407–3411.
Subbarao et al. (1992) "A General Overview of Viral Vaccine Development," *Genetically Engineered Vaccines* 327:51–57.
Szikora et al. (1990) "Structure of the gene of tum–transplantation antigen P35B presence of a point mutation in the antigenic allele", *EMBO J.* 9(4):1041–1050.
Udono (1993) "Heat shock proteins HSP70, HSP90 and GP96 elicit tumor specific immunity to the tumors from which they are isolated", *J. Cell. Biochem.* Suppl. 17D:113 (Abstract NZ225).
Udono et al. (1993) "Heat Shock Protein 70–associated Peptides Elicit Specific Cancer Immunity", *J. Exp. Med.* 178:1391–1396.
Ullrich et al. (1986) "A mouse tumor–specific transplantation antigen is a heat shock–related protein", *Proc. Natl. Acad. Sci. USA* 83:3121–3125.
Vanbuskirk et al. (1989) "peptide binding protein having a role in antigen presentation is a member of the hsp70 heat shock family", *J. Exp. Med.* 170:1799–1809.

Welch et al. (1982), "Purification of the Major Mammalian Heat Shock Proteins", *J. Biol. Chem.* 257:14949–14959.

Welch et al. (1985) "Rapid Purification of Mammalian 70,000–Dalton Stress Proteins: Affinity of the Proteins for Nucleotides", *Mol. Cell. Biol.* 5:1229–1237.

Welch (1993) "How Cells Respond to Stress", *Scientific American* pp. 56–64.

Young (1990) "Stress Proteins and Immunology", *Annu. Rev. Immunol.* 8:401–420.

Yu et al. (1991) "Sequence Analysis of Peptides Bound to MHC Class II Molecules", *Nature* 353:622–627.

Blachere et al. (Mar. 1993) "Immunization with GP96 heat shock proteins isolated from tumors or influenza virus infected cells elicits MHC–restricted, antigen–specific cytotoxic T lymphocytes against the corresponding cells/antigens", *J Cell Biochem Suppl* 17D:124 (Abstract NZ 502).

Srivastava et al. (Mar. 1993) "Evidence for peptide–chaperoning by the endoplasmic reticular heat shock protein GP96: Implications for vaccination against cancer and infectious disease", *J Cell Biochem Suppl* 17D:94 (Abstract NZ014).

Thomas et al. (1982) "Molecular and Cellular Effects of Heat Shock and Related Treatments of Mammalian Tissue–Culture Cells", *Cold Springs Harbor Symp Quant Biol* 46:985–996.

Levinson et al. (1979) "Metal Binding Drugs Induce Synthesis of Four Proteins in Normal Cells", *Biol Trace Element Research* 1:15–23.

Martin et al., (1986) "Role of Murine Tumor Models in Cancer Treatment Research", Cancer Research 46:2189–2192.

Nieland et al., (1996) "Isolation of an immunodominant viral peptide that is endogeneously bound to the stress protein GP96/GRP94", Proc. Natl. Acad. Sci. USA 93:6135–6139.

Suto et al., (1995) "A Mechanism for the Specific Immunogenicity of Heat Shock Protein–Chaperoned Peptides", Science 269:1585–1588.

Udono et al., (1994) "Comparison of Tumor–Specific Immunogenicities of Stress–Induced Proteins gp96, hsp90, and hsp70", J. Immunol. 152:5398–5403.

Mulé et al., (1984) "Adoptive Immunotherapy of Established Pulmonary Metastases with LAK Cells and Recombinant Interleukin–2", Science 225:1487–1489.

Barrios et al., (1994) "Heat shock proteins as carrier molevules: in vivo helper effect mediated by *Escherichia coli* GroEl and Dnak proteins requires cross–linking with antigen", Clin Exp. Immunol., 98:229–233.

Barrios et al., (1994) "Specificity of antibodies induced after immunization of mice with the mycobacterial heat shock protein of 65kD", Clin Exp Immunol, 224–228.

Blachere et al., 1998, "Heat Shock Protein–Peptide Complexes, Reconstituted In Vitro, Elicit Peptide–specific Cytotoxic T Lymphocyte Response and Tumor Immunity", J. Exp.Med., 186:1315–1322.

Ciuputu et al., 1998, "Immunization with a Lymphocytic Choriomeningitis Virus Peptide Mixed with Heat Shock Protein 70 Results in Protective Antiviral Immunity and Specific Cytotoxic T Lymphocytes", J. Exp. Med., 187:685–691.

THERAPEUTIC AND PROPHYLACTIC METHODS USING HEAT SHOCK PROTEINS

This is a division of application Ser. No. 08/527,547, filed Sep. 13, 1995 now U.S. Pat. No. 5,935,576, which is incorporated by reference herein in its entirety.

This invention was made with government support under grant number CA44786 awarded by the National Institutes of Health. The government has certain rights in the invention.

1. INTRODUCTION

The present invention relates to compositions for the prevention and treatment of primary and metastatic cancers and/or infectious diseases. In the practice of the preventive and therapeutic methods of the invention, compositions of noncovalent complexes of heat shock/stress proteins (hsp) including, but not limited to, hsp70, hsp90, gp96 alone or in combination with each other, and antigenic molecules are used to augment the immune responses to genotoxic and nongenotoxic factors, tumors, pathogens and infectious agents.

2. BACKGROUND OF THE INVENTION

Studies on the cellular response to heat shock and other physiological stresses have identified important families of proteins that are involved not only in cellular protection against these aggressions, but also in essential biochemical and immunological processes in unstressed cells. The heat shock proteins include, but are not limited to hsp70, hsp90, gp96, and hsp100; these hsp families accomplish different kinds of chaperoning functions. For example, hsp70, located in the cell cytoplasm, nucleus, mitochondria, or endoplasmic reticulum, (Lindquist, S., et al., 1988, Ann. Rev. Genetics 22:631–677) are involved in the presentation of antigens to the cells of the immune system, and are also involved in the transfer, folding and assembly of proteins in normal cells. Similarly, Hsp90 located in the cytosol are involved in chaperoning and gp96 present in the endoplasmic reticulum are involved in antigen presentation (Srivastava, P. K., et al., 1991, Curr. Topics in Microbiology & Immun. 167:109–123).

2.1. Immunotherapy

In modern medicine, immunotherapy or vaccination has virtually eradicated diseases such as polio, tetanus, tuberculosis, chicken pox, measles, hepatitis, etc. The approach using vaccinations has exploited the ability of the immune system to prevent infectious diseases. Such vaccination with non-live materials such as proteins generally leads to an antibody response or CD4+ helper T cell response. Raychaudhuri, S. and Morrow, W. J. W., 1993, Immunology Today, 14:344–348. On the other hand, vaccination or infection with live materials such as live cells or infectious viruses generally leads to a CD8+ cytotoxic T-lymphocyte (CTL) response. A CTL response is crucial for protection against cancers, infectious viruses and bacteria. This poses a practical problem, for, the only way to achieve a CTL response is to use live agents which are themselves pathogenic. The problem is generally circumvented by using attenuated viral and bacterial strains or by killing whole cells which can be used for vaccination. These strategies have worked well but the use of attenuated strains always carries the risk that the attenuated agent may recombine genetically with host DNA and turn into a virulent strain. Thus, there is need for methods which can lead to CD8+ CTL response by vaccination with non-live materials such as proteins in a specific manner.

The era of tumor immunology began with experiments by Prehn and Main, who showed that antigens on the methylcholanthrene (MCA)-induced sarcomas were tumor specific in that transplantation assays could not detect these antigens in normal tissue of the mice (Prehn, R. T., et al., 1957, J. Natl. Cancer Inst. 18:769–778). This notion was confirmed by further experiments demonstrating that tumor specific resistance against MCA-induced tumors can be elicited in the autochthonous host, that is, the mouse in which the tumor originated (Klein, G., et al., 1960, Cancer Res. 20:1561–1572).

In subsequent studies, tumor specific antigens were also found on tumors induced with other chemical or physical carcinogens or on spontaneous tumors (Kripke, M. L., 1974, J. Natl. Cancer Inst. 53:1333–1336; Vaage, J., 1968, Cancer Res. 28:2477–2483; Carswell, E. A., et al., 1970, J. Natl. Cancer Inst. 44:1281–1288). Since these studies used protective immunity against the growth of transplanted tumors as the criterion for tumor specific antigens, these antigens are also commonly referred to as "tumor specific transplantation antigens" or "tumor specific rejection antigens." Several factors can greatly influence the immunogenicity of the tumor induced, including, for example, the specific type of carcinogen involved, immunocompetence of the host and latency period (Old, L. J., et al., 1962, Ann. N.Y. Acad. Sci. 101:80–106; Bartlett, G. L., 1972, J. Natl. Cancer Inst. 49:493–504).

Most, if not all, carcinogens are mutagens which may cause mutation, leading to the expression of tumor specific antigens (Ames, B. N., 1979, Science 204:587–593; Weisburger, J. H., et al., 1981, Science 214:401–407). Some carcinogens are immunosuppressive (Malmgren, R. A., et al., 1952, Proc. Soc. Exp. Biol. Med. 79:484–488). Experimental evidence suggests that there is a constant inverse correlation between immunogenicity of a tumor and latency period (time between exposure to carcinogen and tumor appearance) (Old, L. J., et al., 1962, Ann. N.Y. Acad. Sci. 101:80–106; and Bartlett, G. L., 1972, J. Natl. Cancer Inst. 49:493–504). Other studies have revealed the existence of tumor specific antigens that do not lead to rejection, but, nevertheless, can potentially stimulate specific immune responses (Roitt, I., Brostoff, J and Male, D., 1993, Immunology, 3rd ed., Mosby, St. Louis, pp. 17.1–17.12).

2.2. Tumor-specific Immunogenicities of Heat Shock/Stress Proteins hsp70, hsp90 and gp96

Srivastava et al. demonstrated immune response to methylcholanthrene-induced sarcomas of inbred mice (1988, Immunol. Today 9:78–83). In these studies it was found that the molecules responsible for the individually distinct immunogenicity of these tumors were identified as cell-surface glycoproteins of 96 kDa (gp96) and intracellular proteins of 84 to 86 kDa (Srivastava, P. K., et al., 1986, Proc. Natl. Acad. Sci. USA 83:3407–3411; Ullrich, S. J., et al., 1986, Proc. Natl. Acad. Sci. USA 83:3121–3125. Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counterparts of the same heat shock proteins (Srivastava, P. K., et al., 1988, Immunogenetics 28:205–207; Srivastava, P. K., et al., 1991, Curr. Top. Microbiol. Immunol. 167:109–123). Further, hsp70 was shown to elicit immunity to the tumor from which it was isolated but not to antigenically distinct tumors. However, hsp70 depleted of peptides was found to lose its immunogenic activity (Udono, M., and Srivastava, P. K., 1993, *J. Exp. Med.* 178:1391–1396). These observations suggested that the heat shock proteins are not immunogenic per se, but are carriers of antigenic peptides that elicit specific immunity to cancers (Srivastava, P. K., 1993, *Adv. Cancer Res.* 62:153–177).

2.3. Pathobiology of Cancer

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins and Angell, 1976, *Basic Pathology,* 2d Ed., W.B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

The neoplastic lesion may evolve clonally and develop an increasing capacity for invasion, growth, metastasis, and heterogeneity, especially under conditions in which the neoplastic cells escape the host's immune surveillance (Roitt, I., Brostoff, J and Kale, D., 1993, Immunology, 3rd ed., Mosby, St. Louis, pps. 17.1–17.12).

3. SUMMARY OF THE INVENTION

The present invention provides pharmaceutical compositions, methods, and kits for prevention and treatment of cancer and/or infectious diseases by enhancing the host's immunocompetence and activity of immune effector cells. The pharmaceutical compositions of the invention comprise complexes of hsps noncovalently bound to exogenous antigenic molecules. The exogenous antigenic molecules differ from the peptides endogenously complexed with hsps in vivo and which copurify with the hsps. The exogenous antigenic molecules are antigens/immunogens or antigenic/immunogenic fragments or derivatives thereof. Such antigenic molecules can be selected from among those known in the art or assayed by the ability to bind to antibody or MHC molecule (antigenicity) or generate immune response (immunogenicity) by standard immunoassays known in the art. The antigenic molecules are noncovalently complexed with hsps in vitro prior to administration to a patient. For treatment or prevention of cancer, the antigenic molecules are molecules that will induce an immune response against the cancer, e.g., tumor-specific antigens, or tumor-associated antigens, preferably of human tumors. For treatment or prevention of infectious diseases, the antigenic molecules are molecules that will induce an immune response against the infectious agent, e.g., antigens of viruses, bacteria, fungi, parasites etc., preferably agents that infect humans. In a specific embodiment, the pharmaceutical compositions of the present invention include hsps complexed not only to a single antigen but also more than one antigen or an entire cocktail of (e.g., tumor specific) antigens. Preferably, the patient is a human, and the hsps are human hsps. The hsps in the complexes can be autologous or allogeneic to the patient.

Particular compositions of the invention and their properties are described in the sections and subsections which follow. Preferably, the complex of hsp and antigenic molecules comprises hsp70, hsp90, gp96, or a combination thereof.

In another embodiment, the pharmaceutical compositions further comprise effective amounts of a biological response modifier, including but not limited to the cytokines interferon-α (IFN-α), IFN-γ, interleukin-2 (IL-2), IL-4, IL-6, tumor necrosis factor (TNF), or other cytokine growth factor.

4. BRIEF DESCRIPTION OF THE DRAWINGS

FIG. 1. Effect of administration of hsp70 complexed with ovalbumin or cytotoxicity of T cells against the EG7 cell line (expresses ovalbumin antigen) or the EL4 cell line (negative for ovalbumin antigen).

Figure 1B:
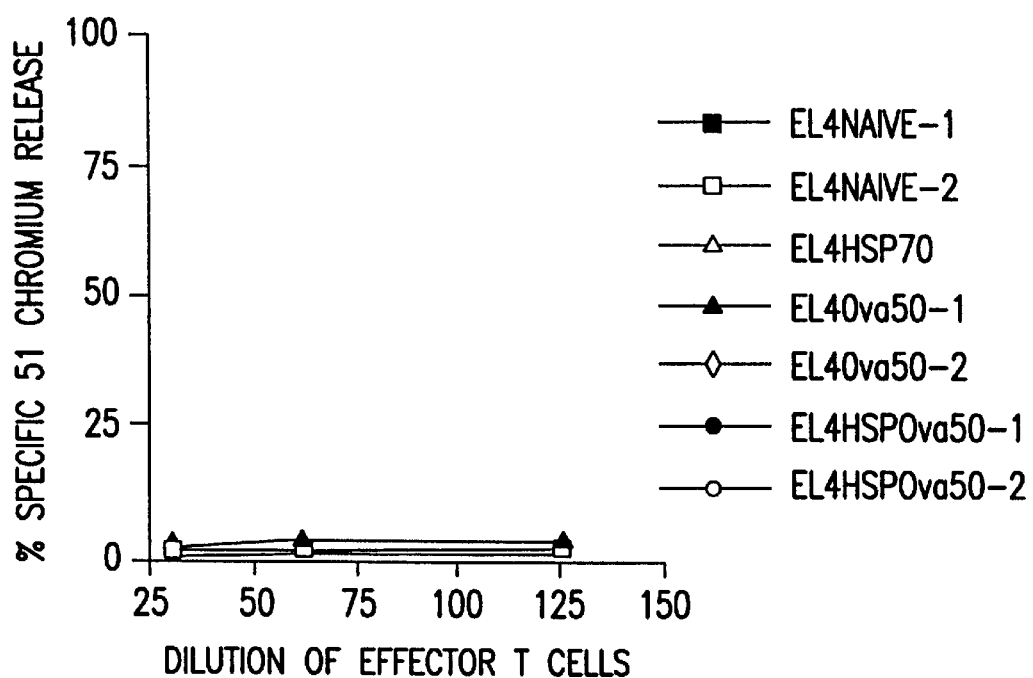

FIG. 1A: Two mice in each group were immunized with: a) a control vehicle (squares); b) ovalbumin alone (plus sign); c) hsp70 alone (triangles); or d) hsp70-ovalbumin complex. T cells taken from the immunized mice were tested for cytotoxicity against the EG7 cells (FIG. 1A) or EL4 cells (FIG. 1B). The results demonstrate that the hsp70-ovalbumin complex is a far better reagent at inducing a cytotoxic T-lymphocyte response than ovalbumin alone or hsp70 alone (FIG. 1A). The T cells did not respond in the presence of the EL4 cells which lack the ovalbumin antigen (FIG. 1B).

5. DETAILED DESCRIPTION OF THE INVENTION

Compositions and methods for the prevention and treatment of primary and metastatic cancers and/or infectious diseases are described. The invention provides pharmaceutical compositions of hsp noncovalently bound to exogenous antigenic molecules.

The exogenous antigenic molecules differ from the peptides endogenously complexed with hsps in vivo and which copurify with the hsps. The exogenous antigenic molecules are antigens/immunogens or antigenic/immunogenic fragments or derivatives thereof. Such antigenic molecules can be selected from among those known in the art or assayed by the ability to bind to antibody or MHC molecule (antigenicity) or generate immune response (immunogenicity) by standard immunoassays known in the art. The antigenic molecules are noncovalently complexed with hsps in vitro prior to administration to a patient. For treatment or prevention of cancer, the antigenic molecules are molecules that will induce an immune response against the cancer, e.g., tumor-specific antigens, or tumor-associated antigens, preferably of human tumors. For treatment or prevention of infectious diseases, the antigenic molecules are molecules that will induce an immune response against the infectious agent, e.g., antigens of viruses, bacteria, fungi, parasites etc., preferably agents that infect humans. In a specific embodiment, the pharmaceutical compositions of the present invention include hsps complexed not only to a single antigen but also more than one antigen or an entire cocktail of (e.g., tumor specific) antigens. Preferably, the patient is a human, and the hsps are human hsps. The hsps in the complexes can be autologous or allogeneic to the patient.

The methods of the invention comprise methods of eliciting an immune response in an individual in whom the treatment or prevention of infectious diseases or cancer is desired by administering a composition comprising an effective amount of a complex, in which the complex consists essentially of a hsp noncovalently bound to an exogenous antigenic molecule. The hsp and/or the antigenic molecule can be isolated from the individual or from others or by recombinant production methods using a cloned hsp originally derived from the individual or from others. Exogenous antigens and fragments and derivatives (both peptide and non-peptide) thereof for use in complexing with hsps, can be selected from among those known in the art, as well as those readily identified by standard immunoassays know in the art by the ability to bind antibody or MHC molecules (antigenicity) or generate immune responses (immunogenicity).

The hsps of the present invention that can be used include but are not limited to, hsp70, hsp90, gp96 alone or in combination. Preferably, the hsps are human hsps.

Heat shock proteins, which are also referred to interchangeably herein as stress proteins, useful in the practice of the instant invention can be selected from among any cellular protein that satisfies any one of the following criteria. It is a protein whose intracellular concentration increases when a cell is exposed to a stressful stimuli, it is capable of binding other proteins or peptides, and it is capable of releasing the bound proteins or peptides in the presence of adenosine triphosphate (ATP) or low pH; or it is a protein showing at least 35% homology with any cellular protein having any of the above properties.

The first stress proteins to be identified were the heat shock proteins (hsps). As their name implies, hsps are synthesized by a cell in response to heat shock. To date, three major families of hsp have been identified based on molecular weight. The families have been called hsp60, hsp70 and hsp90 where the numbers reflect the approximate molecular weight of the stress proteins in kilodaltons. Many members of these families were found subsequently to be induced in response to other stressful stimuli including, but not limited to, nutrient deprivation, metabolic disruption, oxygen radicals, and infection with intracellular pathogens. (See Welch, May 1993, *Scientific American* 56–64; Young, 1990, *Annu. Rev. Immunol.* 8:401–420; Craig, 1993, *Science* 260:1902–1903; Gething, et al., 1992, *Nature* 355:33–45; and Lindquist, et al., 1988, *Annu. Rev. Genetics* 22:631–677), the disclosures of which are incorporated herein by reference.

It is contemplated that hsps/stress proteins belonging to all of these three families can be used in the practice of the instant invention.

The major hsps can accumulate to very high levels in stressed cells, but they occur at low to moderate levels in cells that have been stressed. For example, the highly inducible mammalian hsp70 is hardly detectable at normal temperatures but becomes one of the most actively synthesized proteins in the cell upon heat shock (Welch, et al., 1985, *J. Cell. Biol.* 101:1198–1211). In contrast, hsp90 and hsp60 proteins are abundant at normal temperatures in most, but not all, mammalian cells and are further induced by heat (Lai, et al., 1984, *Mol. Cell. Biol.* 4:2802–10; van Bergen en Henegouwen, et al., 1987, *Genes Dev.* 1:525–31).

Heat shock proteins are among the most highly conserved proteins in existence. For example, DnaK, the hsp70 from *E. coli* has about 50% amino acid sequence identity with hsp70 proteins from excoriates (Bardwell, et al., 1984, *Proc. Natl. Acad. Sci.* 81:848–852). The hsp60 and hsp90 families also show similarly high levels of intra families conservation (Hickey, et al., 1989, *Mol. Cell. Biol.* 9:2615–2626; Jindal, 1989, *Mol. Cell. Biol.* 9:2279–2283). In addition, it has been discovered that the hsp60, hsp70 and hsp90 families are composed of proteins that are related to the stress proteins in sequence, for example, having greater than 35% amino acid identity, but whose expression levels are not altered by stress. Therefore it is contemplated that the definition of stress protein, as used herein, embraces other proteins, muteins, analogs, and variants thereof having at least 35% to 55%, preferably 55% to 75%, and most preferably 75% to 85% amino acid identity with members of the three families whose expression levels in a cell are enhanced in response to a stressful stimulus. The purification of stress proteins belonging to these three families is described below.

The immunogenic complexes of hsp and exogenous antigenic molecules of the invention include any complex containing an hsp and an exogenous antigenic molecule that is capable of inducing an immune response in a mammal. The antigenic molecules are noncovalently associated with the hsps. Preferred complexes comprise hsp60, hsp70, or hsp90, noncovalently bound to a protein antigen. In a specific embodiment, the complex comprises an hsp called gp96 which is present in the endoplasmic reticulum of eukaryotic cells and is related to the cytoplasmic hsp90s.

Although the hsps can be allogeneic to the patient, in a preferred embodiment, the hsps are autologous to (derived from) the patient to whom they are administered. The hsps and/or antigenic molecules can be purified from natural sources, chemically synthesized, or recombinantly produced. The invention provides methods for determining doses for human cancer immunotherapy by evaluating the optimal dose of hsp noncovalently bound to peptide complexes in experimental tumor models and extrapolating the data. Specifically, a scaling factor not exceeding a fifty fold increase over the effective dose estimated in animals, is used as the optimal prescription method for cancer immunotherapy or vaccination in human subjects.

The invention provides compositions comprising the hsp-antigenic molecule complexes which enhance the immunocompetence of the host individual and elicit specific immunity against infectious agents or specific immunity against preneoplastic and neoplastic cells. The therapeutic regimens and pharmaceutical compositions of the invention are described below. These compositions are believed to have the capacity to prevent the onset and progression of infectious diseases and prevent the development of tumor cells and to inhibit the growth and progression of tumor cells indicating that such compositions can induce specific immunity in infectious diseases and cancer immunotherapy.

The complexes of the invention can be used to induce an inflammatory reaction at the tumor site and ultimately cause a regression of the tumor burden in the cancer patients treated. Cancers which can be treated with complexes of hsps noncovalently bound to exogenous antigenic molecules include, but are not limited to, human sarcomas and carcinomas.

Accordingly, the invention provides methods of preventing and treating cancer in an individual comprising administering a composition which stimulates the immunocompetence of the host individual and elicits specific immunity against the preneoplastic and/or neoplastic cells. As used herein, "preneoplastic" cell refers to a cell which is in transition from a normal to a neoplastic form; and morphological evidence, increasingly supported by molecular biologic studies, indicates that preneoplasia progresses through multiple steps. Non-neoplastic cell growth commonly consists of hyperplasia, metaplasia, or most particularly, dysplasia (for review of such abnormal growth conditions (See Robbins and Angell, 1976, *Basic Pathology*, 2d Ed., W.B. Saunders Co., Philadelphia, pp. 68–79).

The therapeutic regimens and pharmaceutical compositions of the invention may be used with additional immune response enhancers or cytokines including, but not limited to, the cytokines IFN-α, IFN-γ, IL-2, IL-4, IL-6, TNF, or other cytokine affecting immune cells. In accordance with this aspect of the invention, the complexes of the hsp and antigenic molecule are administered in combination therapy with one or more of these cytokines.

The invention further relates to administration of complexes of hsp-antigenic molecules to individuals at enhanced risk of cancer due to familial history or environmental risk factors.

The compositions comprising hsp noncovalently bound to exogenous antigenic molecules are administered to elicit an effective specific immune response to the complexed antigenic molecules (and not to the hsp).

In a preferred embodiment, hsp70, hsp90 and/or gp96 are noncovalently complexed with exogenous antigenic molecules.

In accordance with the methods described herein, the exogenous antigenic molecules are immunogenic or antigenic proteins or other molecules or immunogenic/antigenic fragments or derivatives thereof. For example, exogenous antigenic molecules include but are nbt limited to different tumor specific translatable antigens (e.g., tyrosinase, gp100, melan-A, gp75, mucins, etc.) and viral antigens including, but not limited to, proteins of immunodeficiency virus type I (HIV-I), human immunodeficiency virus type II (HIV-II), hepatitis type A, hepatitis type B, hepatitis type C, influenza, Varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus and polio virus.

In a specific embodiment, antigens of cancers (e.g., tumors) or infectious agents (e.g., viral antigen, bacterial antigens, etc.) can be obtained by purification from natural sources, by chemical synthesis, or recombinantly, and, through in vitro procedures such as that described below, noncovalently complexed to hsps.

5.1. Purification of Hsps

In an embodiment wherein the hsp portion of the hsp-antigenic molecule complex is desired to be purified from cells, exemplary purification procedures such as described in Sections 5.1.1–5.1.3 below can be employed to purify hsp-peptide complexes, after which the hsps can be purified from the endogenous hsp-peptide complexes in the presence of ATP or low pH, for subsequent in vitro complexing to exogenous antigenic molecules. Although described for tumor cells, the protocols described hereinbelow may be used to isolate hsps from any eukaryotic cells, for example, tissues, isolated cells, or immortalized eukaryote cell lines infected with a preselected intracellular pathogen, tumor cells or tumor cell lines.

Alternatively to isolation of native hsps from cells as described in Sections 5.1.1–5.1.3, hsps can be chemically synthesized or recombinantly produced.

5.1.1. Preparation and Purification of Hsp70-peptide Complexes

The purification of hsp70-peptide complexes has been described previously, see, for example, Udono et al., 1993, *J. Exp. Med.* 178:1391–1396. A procedure that may be used, presented by way of example but not limitation, is as follows:

Initially, tumor cells are suspended in 3 volumes of 1×Lysis buffer consisting of 5 mM sodium phosphate buffer (pH 7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with phosphate buffered saline (PBS) containing 2 mM $Ca^{2+}$ and 2 mM $Mg^{2+}$. When the cells are lysed by mechanical shearing the supernatant is diluted with an equal volume of 2×lysis buffer prior to mixing with Con A Sepharose. The supernatant is then allowed to bind to the Con A Sepharose for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC column equilibrated in 20 mM TrisAcetate pH 7.5, 20 mM NaCl, 0.1 mM EDTA and 15 mM 2-mercaptoethanol. The column is then developed with a 20 mM to 500 mM NaCl gradient and then eluted fractions fractionated by sodium dodecyl sulfate-polyacrylamide gel electrophoresis (SDS-PAGE) and characterized by immunoblotting using an appropriate anti-hsp70 antibody (such as from clone N27F3-4, from StressGen).

Fractions strongly immunoreactive with the anti-hsp70 antibody are pooled and the hsp70-peptide complexes precipitated with ammonium sulfate; specifically with a 50%–70% ammonium sulfate cut. The resulting precipitate is then harvested by centrifugation at 17,000 rpm (SS34 Sorvall rotor) and washed with 70% ammonium sulfate. The washed precipitate is then solubilized and any residual ammonium sulfate removed by gel filtration on a Sephadex$^R$ G25 column (Pharmacia). If necessary the hsp70 preparation thus obtained can be repurified through the Mono Q FPCL Column as described above.

The hsp70-peptide complex can be purified to apparent homogeneity using this method. Typically 1 mg of hsp70-peptide complex can be purified from 1 g of cells/tissue.

The present invention further describes a new and rapid method for purification of hsp70. This improved method uses column chromatography with ATP affixed to a solid substratum (e.g., ATP-agarose). The hsp70 yields are believed to be increased significantly and have high purity. By way of example but not limitation, purification of hsp70 by ATP-agarose chromatography was carried out as follows: Meth A sarcoma cells (500 million cells) were homogenized in hypotonic buffer and the lysate was centrifuged at 100,000 g for 90 minutes at 4° C. The supernatant was divided into two and was applied to an ADP-agarose or an ATP-agarose column. The columns were washed in buffer and were eluted with 3 mM ADP or 3 mM ATP, respectively. The eluted fractions were analyzed by SDS-PAGE: in both cases, apparently homogeneous preparations of hsp70 were obtained. However, when each of the preparations was tested for presence of peptides, the ADP-bound/eluted hsp70 preparation was found to be associated with peptides, while the ATP-bound/eluted hsp70 preparation was not.

5.1.2. Preparation and Purification of Hsp90-peptide Complexes

A procedure that can be used, presented by way of example and not limitation, is as follows:

Initially, tumor cells are suspended in 3 volumes of 1×Lysis buffer consisting of 5 mM sodium phosphate buffer (pH 7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with PBS containing 2 mM $Ca^{2+}$ and 2 mM $Mg^{2+}$. When the cells are lysed by mechanical shearing the supernatant is diluted with an equal volume of 2×lysis buffer prior to mixing with Con A Sepharose. The supernatant is then allowed to bind to the Con A Sepharose for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC column equilibrated with lysis buffer. The proteins are then eluted with a salt gradient of 200 mM to 600 mM NaCl.

The eluted fractions are fractionated by SDS-PAGE and fractions containing the hsp90-peptide complexes identified by immunoblotting using an anti-hsp90 antibody such as 3G3 (Affinity Bioreagents). Hsp90-peptide complexes can be purified to apparent homogeneity using this procedure. Typically, 150–200 $\mu$g of hsp90-peptide complex can be purified from 1 g of cells/tissue.

5.1.3. Preparation and Purification of gp96-peptide Complexes

A procedure that can be used, presented by way of example and not limitation, is as follows:

A pellet of tumors is resuspended in 3 volumes of buffer consisting of 30 mM sodium bicarbonate buffer (pH 7.5) and 1 mM PMSF and the cells allowed to swell on ice 20 minutes. The cell pellet then is homogenized in a Dounce homogenizer (the appropriate clearance of the homogenizer will vary according to each cells type) on ice until >95% cells are lysed.

The lysate is centrifuged at 1,000 g for 10 minutes to remove unbroken cells, nuclei and other debris. The supernatant from this centrifugation step then is recentrifuged at 100,000 g for 90 minutes. The gp96-peptide complex can be purified either from the 100,000 pellet or from the supernatant.

When purified from the supernatant, the supernatant is diluted with equal volume of 2×lysis buffer and the supernatant mixed for 2–3 hours at 4° C. with Con A Sepharose equilibrated with PBS containing 2 mM $Ca^{2+}$ and 2 mM $Mg^{2+}$. Then, the slurry is packed into a column and washed with 1×lysis buffer until the $OD_{280}$ drops to baseline. Then, the column is washed with ⅓ column bed volume of 10% α-methyl mannoside (α-MM) dissolved in PBS containing 2 mM $Ca^{2+}$ and 2 mM $Mg^{2+}$, the column sealed with a piece of parafilm, and incubated at 37° C. for 15 minutes. Then the column is cooled to room temperature and the parafilm removed from the bottom of the column. Five column volumes of the α-MM buffer are applied to the column and the eluate analyzed by SDS-PAGE. Typically the resulting material is about 60–95% pure, however this depends upon the cell type and the tissue-to-lysis buffer ratio used. Then the sample is applied to a Mono Q FPLC column (Pharmacia) equilibrated with a buffer containing 5 mM sodium phosphate, pH 7. The proteins then are eluted from the column with a 0–1M NaCl gradient and the gp96 fraction elutes between 400 mM and 550 mM NaCl.

The procedure, however, may be modified by two additional steps, used either alone or in combination, to consistently produce apparently homogeneous gp96-peptide complexes. One optional step involves an ammonium sulfate precipitation prior to the Con A purification step and the other optional step involves DEAE-Sepharose purification after the Con A purification step but before the Mono Q FPLC step.

In the first optional step, the supernatant resulting from the 100,000 g centrifugation step is brought to a final concentration of 50% ammonium sulfate by the addition of ammonium sulfate. The ammonium sulfate is added slowly while gently stirring the solution in a beaker placed in a tray of ice water. The solution is stirred from about ½ to 12 hours at 4° C. and the resulting solution centrifuged at 6,000 rpm (Sorvall SS34 rotor). The supernatant resulting from this step is removed, brought to 70% ammonium sulfate saturation by the addition of ammonium sulfate solution, and centrifuged at 6,000 rpm (Sorvall SS34 rotor). The resulting pellet from this step is harvested and suspended in PBS containing 70% ammonium sulfate in order to rinse the pellet. This mixture is centrifuged at 6,000 rpm (Sorvall SS34 rotor) and the pellet dissolved in PBS containing 2 mM $Ca^{2+}$ and $Mg^{2+}$. Undissolved material is removed by a brief centrifugation at 15,000 rpm (Sorvall SS34 rotor). Then, the solution is mixed with Con A Sepharose and the procedure followed as before.

In the second optional step, the gp96 containing fractions eluted from the Con A column are pooled and the buffer exchanged for 5 mM sodium phosphate buffer, pH 7,300 mM NaCl by dialysis, or preferably by buffer exchange on a Sephadex G25 column. After buffer exchange, the solution is mixed with DEAE-Sepharose previously equilibrated with 5 mM sodium phosphate buffer, pH 7, 300 mM NaCl. The protein solution and the beads are mixed gently for 1 hour and poured into a column. Then, the column is washed with 5 mM sodium phosphate buffer, pH 7, 300 mM NaCl, until the absorbance at 280 nM drops to baseline. Then, the bound protein is eluted from the column with five volumes of 5 mM sodium phosphate buffer, pH 7, 700 mM NaCl. Protein containing fractions are pooled and diluted with 5 mM sodium phosphate buffer, pH 7 in order to lower the salt concentration to 175 mM. The resulting material then is applied to the Mono Q FPLC column (Pharmacia) equilibrated with 5 mM sodium phosphate buffer, pH 7 and the protein that binds to the Mono Q FPLC column (Pharmacia) is eluted as described before.

It is appreciated, however, that one skilled in the art may assess, by routine experimentation, the benefit of incorporating the second optional step into the purification protocol. In addition, it is appreciated also that the benefit of adding each of the optional steps will depend upon the source of the starting material.

When the gp96 fraction is isolated from the 100,000 g pellet, the pellet is suspended in 5 volumes of PBS containing either 1% sodium deoxycholate or 1% oxtyl glucopyranoside (but without the $Mg^{2+}$ and $Ca^{2+}$) and incubated on ice for 1 hour. The suspension is centrifuged at 20,000 g for 30 minutes and the resulting supernatant dialyzed against several changes of PBS (also without the $Mg^{2+}$ and $Ca^{2+}$) to remove the detergent. The dialysate is centrifuged at 100,000 g for 90 minutes, the supernatant harvested, and calcium and magnesium are added to the supernatant to give final concentrations of 2 mM, respectively. Then the sample is purified by either the unmodified or the modified method for isolating gp96-peptide complex from the 100,000 g supernatant, see above.

The gp96-peptide complexes can be purified to apparent homogeneity using this procedure. About 10–20 μg of gp96 can be isolated from 1 g cells/tissue.

5.2 Exogenous Antigenic Molecules 5.2.1. Peptides from MHC Complexes

It has been found that potentially immunogenic peptides may be eluted from MHC-peptide complexes using techniques well known in the art (Falk, K. et al., 1990 *Nature* 348:248–251; Elliott, T., et al., 1990, *Nature* 348:195–197; Falk, K., et al., 1991, *Nature* 351:290–296). Once isolated, the amino acid sequence of each antigenic peptide may be determined using conventional amino acid sequencing methodologies. Such antigenic molecules can then be produced by chemical synthesis or recombinant methods, purified, and complexed to hsps in vitro.

Thus, potentially immunogenic or antigenic peptides may be isolated from endogenous MHC-peptide complexes for use subsequently as exogenous antigenic molecules, by complexing in vitro to hsps. Exemplary protocols for isolating peptides and/or antigenic components from MHC complexes are set forth below in Section 5.2.1.1.

5.2.1.1. Peptides from MHC-peptide Complexes

The isolation of potentially immunogenic peptides from MHC molecules is well known in the art and so is not described in detail herein (See, Falk, et al., 1990, *Nature* 348:248–251; Rotzsche, at al., 1990, *Nature* 348:252–254; Elliott, et al., 1990, *Nature* 348:191–197; Falk, et al., 1991, *Nature* 351:290–296; Demotz, et al., 1989, *Nature* 343:682–684; Rotzsche, et al., 1990, *Science* 249:283–287), the disclosures of which are incorporated herein by reference.

Briefly, MHC-peptide complexes may be isolated by a conventional immunoaffinity procedure. The peptides then may be eluted from the MHC-peptide complex by incubating the complexes in the presence of about 0.1% TFA in acetonitrile. The eluted peptides may be fractionated and purified by reverse phase HPLC, as before.

The amino acid sequences of the eluted peptides may be determined either by manual or automated amino acid sequencing techniques well known in the art. Once the amino acid sequence of a potentially protective peptide has been determined the peptide may be synthesized in any desired amount using conventional peptide synthesis or other protocols well known in the art.

Peptides having the same amino acid sequence as those isolated above may be synthesized by solid-phase peptide synthesis using procedures similar to those described by Merrifield, 1963, *J. Am. Chem. Soc.,* 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile.

Briefly, the C-terminal N-α-protected amino acid is first attached to the polystyrene beads. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton, et al., 1989, *Solid Phase Peptide Synthesis: A Practical Approach,* IRL Press, and Bodanszky, 1993, *Peptide Chemistry, A Practical Textbook,* 2nd Ed., Springer-Verlag).

Purification of the resulting peptides is accomplished using conventional procedures, such as preparative HPLC using gel permeation, partition and/or ion exchange chromatography. The choice of appropriate matrices and buffers are well known in the art and so are not described in detail herein.

5.2.2. Other Exogenous Antigenic Molecules

Antigens or antigenic portions thereof can be selected for use as antigenic molecules, for complexing to hsps, from among those known in the art or determined by immunoassay to be able to bind to antibody or MHC molecules (antigenicity) or generate immune responses (immunogenicity). To determine immunogenicity or antigenicity by detecting binding to antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in vivo immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are envisioned for use. In one embodiment for detecting immunogenicity, T cell-mediated responses can be assayed by standard methods, e.g., in vitro cytoxicity assays or in vivo delayed-type hypersensitivity assays.

Potentially useful antigens or derivatives thereof for use as antigenic molecules can also be identified by various criteria, such as the antigen's involvement in neutralization of a pathogen's infectivity (wherein it is desired to treat or prevent infection by such a pathogen) (Norrby, 1985, *Summary*, in Vaccines 85, Lerner, et al. (eds.), Cold Spring Harbor Laboratory, Cold Spring Harbor, N.Y., pp. 388–389), type or group specificity, recognition by patients' antisera or immune cells, and/or the demonstration of protective effects of antisera or immune cells specific for the antigen. In addition, where it is desired to treat or prevent a disease caused by pathogen, the antigen's encoded epitope should preferably display a small or no degree of antigenic variation in time or amongst different isolates of the same pathogen.

Preferably, where it is desired to treat or prevent cancer, known tumor-specific antigens or fragments or derivatives thereof are used. For example, such tumor specific or tumor-associated antigens include but are not limited to KS 1/4 pan-carcinoma antigen (Perez and Walker, 1990, *J. Immunol.* 142:3662–3667; Bumal, 1988, *Hybridoma* 7(4):407–415); ovarian carcinoma antigen (CA125) (Yu, et al., 1991, *Cancer Res.* 51(2):468–475); prostatic acid phosphate (Tailer, et al., 1990, *Nucl. Acids Res.* 18(16):4928); prostate specific antigen (Henttu and Vihko, 1989, *Biochem. Biophys. Res. Comm.* 160(2):903–910; Israeli, et al., 1993, *Cancer Res.* 53:227–230); melanoma-associated antigen p97 (Estin, et al., 1989, *J. Natl. Cancer Inst.* 81(6):445–446); melanoma antigen gp75 (Vijayasardahl, et al., 1990, *J. Exp. Med.* 171(4):1375–1380); high molecular weight melanoma antigen (Natali, et al., 1987, *Cancer* 59:55–63) and prostate specific membrane antigen.

In a specific embodiment, an antigen or fragment or derivative thereof specific to a certain tumor is selected for complexing to hsp and subsequent administration to a patient having that tumor.

Preferably, where it is desired to treat or prevent viral diseases, molecules comprising epitopes of known viruses are used. For example, such molecules comprise epitopes from proteins of viruses including, but not limited to, hepatitis type A hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial. virus, papilloma virus, papova virus, cytomegalovirus, echinovirus, arbovirus, huntavirus, coxsachie virus, mumps virus, measles virus, rubella virus, polio virus, human immunodeficiency virus type I (HIV-I), and human immunodeficiency virus type II (HIV-II).

Preferably, where it is desired to treat or prevent bacterial infections, molecules comprising epitopes of known bacteria are used. For example, such antigenic epitopes may be from bacteria including, but not limited to, mycobacteria rickettsia, mycoplasma, neisseria and legionella.

Preferably, where it is desired to treat or prevent protozoal infectious, molecules comprising epitopes of known protozoa are used. For example, such protozoa include, but are not limited to, leishmania, kokzidioa, and trypanosoma.

Preferably, where it is desired to treat or prevent parasitic infectious, molecules comprising epitopes of known parasites are used. For example, such antigenic epitopes may be from parasites including, but not limited to, chlamydia and rickettsia.

5.3. In Vitro Production of Stress Protein-antigenic Molecule Complexes

As will be appreciated by those skilled in the art, exogenous antigenic molecules, either purified from natural sources or chemically synthesized or recombinantly produced, may be reconstituted with a variety of naturally purified or chemically synthesized or recombinantly produced stress proteins in vitro to generate immunogenic noncovalent stress protein-antigenic molecule complexes. A preferred, exemplary protocol for noncovalently complexing a stress protein and an exogenous antigenic molecule in vitro is described below.

Prior to complexing, the hsps are pretreated with ATP or low pH to remove any peptides that may be associated with the hsp of interest. When the ATP procedure is used, excess ATP is removed from the preparation by the addition of apyranase as described by Levy, et al., 1991, *Cell* 67:265–274. When the low pH procedure is used, the buffer is readjusted to neutral pH by the addition of pH modifying reagents.

The antigenic molecules (1 $\mu$g) and the pretreated hsp (9 $\mu$g) are admixed to give an approximately 5 antigenic molecule:1 stress protein molar ratio. Then, the mixture is incubated for 15 minutes to 3 hours at room temperature in a suitable binding buffer such as one containing 20 mM sodium phosphate, pH 7.2, 350 mM NaCl, 3 mM $MgCl_2$ and 1 mM phenyl methyl sulfonyl fluoride (PMSF). The preparations are centrifuged through Centricon 10 assembly (Millipore) to remove any unbound peptide. The association of the peptides with the stress proteins can be assayed by SDS-PAGE. This is the preferred method for in vitro complexing of peptides isolated from MHC-peptide complexes of peptides disassociated from endogenous hsp-peptide complexes.

In an alternative embodiment of the invention, preferred for producing complexes of hsps70 to exogenous antigenic molecules that are proteins, 5–10 micrograms of purified hsp is incubated with equimolar quantities of the antigenic molecule in 20 mM sodium phosphate buffer pH 7.5, 0.5M NaCl, 3 mM $MgCl_2$ and 1 mM ADP in a volume of 100 microliter at 37° C. for 1 hr. This incubation mixture is further diluted to 1 ml in phosphate-buffered saline.

In an alternate embodiment of the invention, preferred for producing complexes of gp96 or hsp90 to peptides 5–10 micrograms of purified gp96 or hsp90 is incubated with equimolar or excess quantities of the antigenic peptide in a suitable buffer such as one containing 20 mM sodium phosphate buffer 7.5, 0.5 m NaCl, 3 mM $MgCl_2$ at 60–65° C. for 5–20 minutes. This incubation mixture is allowed to cool to room temperature and centrifuged more than once if necessary through Centrican 10 assembly (Millipore to remove any unbound peptide).

Following complexing, the immunogenic stress protein-antigenic molecule complexes can optionally be assayed in vitro using for example the mixed lymphocyte target cell assay (MLTC) described below. Once immunogenic complexes have been isolated they can be optionally characterized further in animal models using the preferred administration protocols and excipients discussed below.

5.4. Determination of Immunogenicity of Stress Protein-peptide Complexes

In an optional procedure, the purified stress protein-antigenic molecule complexes can be assayed for immunogenicity using the mixed lymphocyte target culture assay (MLTC) well known in the art.

By way of example but not limitation, the following procedure can be used. Briefly, mice are injected subcutaneously with the candidate stress protein-antigenic molecule complexes. Other mice are injected with either other stress protein peptide complexes or whole infected cells which act as positive controls for the assay. The mice are injected twice, 7–10 days apart. Ten days after the last immunization, the spleens are removed and the lymphocytes released. The released lymphocytes may be restimulated subsequently in vitro by the addition of dead cells that expressed the complex of interest.

For example, 8×10⁶ immune spleen cells may be stimulated with 4×10⁴ mitomycin C treated or γ-irradiated (5–10,000 rads) infected cells (or cells transfected with an appropriate gene, as the case may be) in 3 ml RPMI medium containing 10% fetal calf serum. In certain cases 33% secondary mixed lymphocyte culture supernatant may be included in the culture medium as a source of T cell growth factors (See, Glasebrook, et al., 1980, *J. Exp. Med.* 151:876). To test the primary cytotoxic T cell response after immunization, spleen cells may be cultured without stimulation. In some experiments spleen cells of the immunized mice may also be restimulated with antigenically distinct cells, to determine the specificity of the cytotoxic T cell response.

Six days later the cultures are tested for cytotoxicity in a 4 hour $^{51}$Cr-release assay (See, Palladino, et al., 1987, *Cancer Res.* 47:5074–5079 and Blachere, at al., 1993, *J. Immunotherapy* 14:352–356). In this assay, the mixed lymphocyte culture is added to a target cell suspension to give different effector:target (E:T) ratios (usually 1:1 to 40:1). The target cells are prelabelled by incubating 1×10⁶ target cells in culture mediume containing 200 mCi $^{51}$Cr/ml for one hour at 37° C. The cells are washed three times following labeling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are peletted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

In order to block the MHC class I cascade a concentrated hybridoma supernatant derived from K-44 hybridoma cells (an anti-MHC class I hybridoma) is added to the test samples to a final concentration of 12.5%.

5.5. Formulation

Complexes of the invention (of hsps noncovalently bound to exogenous antigenic molecules) may be formulated into pharmaceutical preparations for administration to mammals for treatment of tumors and infectious diseases. Preferred dosages, routes of administration and therapeutic regimens are described in copending application by P. Srivastava entitled "Compositions and Methods for the Prevention and Treatment of Primary and Metastatic Neoplastic Diseases and Infectious Diseases with Heat Shock/Stress Proteins, filed on even date herewith, which is incorporated by reference herein in its entirety. For example, pharmaceutical formulations are provided, based on a newly-discovered extrapolation and scaling of animal dosage to human, comprising compositions of complexes of antigenic molecules and heat shock/stress proteins, including but not limited to hsp70, hsp90, gp96 either alone or in combination. Specifically, interspecies dose-response equivalence for hsp noncovalently bound to antigenic molecules for a human dose is estimated as the product of the therapeutic dosage observed in mice and a single scaling ratio, not exceeding a 50-fold increase. In preferred aspects, an amount of hsp70- and/or gp96-antigenic molecule complex is administered to a human that is in the range of about 10–600 μg, preferably 10–100 μg, most preferably about 25 μg, given once weekly for about 4–6 weeks, subcutaneously with the site of administration varied sequentially. Preferred amounts for hsp90-antigenic molecule complexes are in the range of 50–5,000 μg, preferably 100 μg.

Compositions comprising a compound of the invention formulated in a compatible pharmaceutical carrier may be prepared, packaged, and labelled for treatment of the indicated tumor, such as human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastqma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease. Alternatively, it can be formulated and labeled for treatment of the appropriate infectious disease.

If the complex is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the hsp-antigenic molecule complexes in pharmaceutically acceptable form. The hsp-antigenic molecule complex in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of hsp-antigenic molecule complexes by a clinician or by the patient.

5.6. Target Infectious Diseases

Infectious diseases that can be treated or prevented by the methods of the present invention are caused by infectious agents including, but not limited to viruses, bacteria, fungi protozoa and parasites.

Viral diseases that can be treated or prevented by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, human immunodeficiency virus type I (HIV-I), and human immunodeficiency virus type II (HIV-II).

Bacterial diseases that can be treated or prevented by the methods of the present invention are caused by bacteria including, but not limited to, mycobacteria rickettsia, mycoplasma, neisseria and legionella.

Protozoal diseases that can be treated or prevented by the methods of the present invention are caused by protozoa including, but not limited to, leishmania, kokzidioa, and trypanosoma.

Parasitic diseases that can be treated or prevented by the methods of the present invention are caused by parasites including, but not limited to, chlamydia and rickettsia.

5.7. Target Cancers

Cancers that can be treated or prevented by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease. Specific examples of such cancers are described in the sections below.

In a specific embodiment the cancer is metastatic. In another specific embodiment, the patient having a cancer is immunosuppressed by reason of having undergone anti-cancer therapy (e.g., chemotherapy radiation) prior to administration of the hsp-antigenic molecule complexes of the invention. In another specific embodiment, the cancer is a tumor.

5.7.1. Colorectal Cancer Metastatic to the Liver

In 1992, approximately 150,000 Americans were diagnosed with colorectal cancer and more than 60,000 died as a result of colorectal metastases. At the time of their deaths, 80 percent of patients with colorectal cancer have metastatic disease involving the liver, and one-half of these patients have no evidence of other (extrahepatic) metastases. Most metastatic tumors of the liver are from gastrointestinal primaries. Unfortunately, the natural history of metastatic liver lesions carries a grave prognosis and systemic chemotherapy regimens have been unable to induce significant response rates or alter length of survival (Drebin, J. A., et al., in *Current Therapy In Oncology*, ed. J. E. Niederhuber, B. C. Decker, Mosby, 1993, p.426).

Colorectal cancer initially spreads to regional lymph nodes and then through the portal venous circulation to the liver, which represents the most common visceral site of metastasis. The symptoms that lead patients with colorectal cancer to seek medical care vary with the anatomical location of the lesion. For example, lesions in the ascending colon frequency ulcerate, which leads to chronic blood loss in the stool.

Radical resection offers the greatest potential for cure in patients with invasive colorectal cancer. Before surgery, the CEA titer is determined. Radiation therapy and chemotherapy are used in patients with advanced colorectal cancer. Results with chemotherapeutic agents (e.g., 5-fluorouracil) are mixed and fewer than 25 percent of patients experience a greater than 50 percent reduction in tumor mass (Richards, 2d., F., et al., 1986, *J. Clin. Oncol.* 4:565).

Patients with widespread metastases have limited survival and systemic chemotherapy has little impact in this group of patients. In addition, systemically administered chemotherapy is often limited by the severity of toxicities associated with the various agents, such as severe diarrhea, mucositis and/or myelosuppression. Other techniques, including hepatic radiation, systemic chemotherapy, hepatic arterial ligation, tumor embolization and immunotherapy have all been explored, but, for the most part, have proven ineffectual in prolonging patient survival.

In a specific embodiment, the present invention provides compositions and methods for enhancing tumor specific immunity in individuals suffering from colorectal cancer metastasized to the liver, in order to inhibit the progression of the neoplastic disease.

Accordingly, as an example of the method of the invention, gp96 is administered to a patient diagnosed with colorectal cancer, with or without liver metastasis, via one of many different routes of administration, the preferred routes being subcutaneous at different anatomical sites, e.g., left arm, right arm, left belly, right belly, left thigh, right thigh, etc. These routes of administration are used in sequence and the site of injection is varied for each weekly injection as described in Section 7. The preparations and use of therapeutically effective compositions for the prevention and treatment of primary and metastatic cancers are described in detail in the sections which follow and by way of example, infra.

5.7.2. Hepatocellular Carcinoma

Hepatocellular carcinoma is generally a disease of the elderly in the United States. Although many factors may lead to hepatocellular carcinoma, the disease is usually limited to those persons with preexisting liver disease. Approximately 60 to 80 percent of patients in the United States with hepatocellular carcinoma have a cirrhotic liver and about four percent of individuals with a cirrhotic liver eventually develop hepatocellular carcinoma (Niederhuber, J. E., (ed.), 1993, *Current Therapy in Oncology*, B. C. Decker, Mosby). The risk is highest in patients whose liver disease is caused by inherited hemochromatosis or hepatic B viral infection (Bradbear, R. A., et al., 1985, *J. Natl. Cancer Inst.* 75:81; Beasley, R. P., et al., 1981, *Lancet* 2:1129). Other causes of cirrhosis that can lead to hepatocellular carcinoma include alcohol abuse and hepatic fibrosis caused by chronic administration of methotrexate. The most frequent symptoms of hepatocellular carcinoma are the development of a painful mass in the right upper quadrant or epigastrium, accompanied by weight loss. In patients with cirrhosis, the development of hepatocellular carcinoma is preceded by ascites, portal hypertension and relatively abrupt clinical deterioration. In most cases, abnormal values in standard liver function tests such as serum aminotransferase and alkaline phosphatase are observed.

CT scans of the liver are used to determine the anatomic distribution of hepatocellular carcinoma and also provide orientation for percutaneous needle biopsy. Approximately 70 percent of patients with hepatocellular carcinoma have an elevated serum alpha-fetoprotein concentration (McIntire, K. R., et al., 1975, *Cancer Res.* 35:991) and its concentration correlates with the extent of the disease.

Radical resection offers the only hope for cure in patients with hepatocellular carcinoma. Such operative procedures are associated with five-year survival rates of 12 to 30 percent. Liver transplantation may improve survival of some younger individuals. However, most patients are not surgical candidates because of extensive cirrhosis multifocal tumor pattern or scarcity of compatible donor organs. Chemotherapeutic agents have been administered either by intravenous route or through an intrahepatic arterial catheter. Such therapy has sometimes been combined with irradiation to the liver. Reductions in the size of measurable tumors of 50% or more have been reported in some patients treated with either systemic doxorubicin or 5-fluorouracil. However, chemotherapy often induces immunosuppression and rarely causes the tumor to disappear completely and the duration of response is short. The prognosis for patients with hepatocellular carcinoma is negatively correlated with cirrhosis and metastases to the lungs or bone. Median survival for patients is only four to six months. In another specific embodiment, the present invention provides compositions and methods for enhancing specific immunity in individuals suffering from hepatocellular carcinoma in order to inhibit the progression of the neoplastic disease and ultimately irradiate all preneoplastic an neoplastic cells.

5.7.3. Breast Cancer

Another specific aspect of the invention relates to the treatment of breast cancer. The American Cancer Society estimated that in 1992 180,000 American women were diagnosed with breast cancer and 46,000 succumbed to the disease (Niederhuber, J. E.ed. *Current Therapy in Oncology* B. C. Decker, Mosby, 1993). This makes breast cancer the second major cause of cancer death in women, ranking just behind lung cancer. A disturbing fact is the observation that breast cancer has been increasing at a rate of 3 percent per year since 1980 (Niederhuber, J. E., ed. *Current Therapy in Oncology*, B. C. Decker, Mosby, (1993)). The treatment of breast cancer presently involves surgery, radiation, hormonal therapy and/or chemotherapy. Consideration of two breast cancer characteristics, hormone receptors and disease extent, has governed how hormonal therapies and standard-dose chemotherapy are sequenced to improve survival and maintain or improve quality of life. A wide range of multi-drug regimens have been used as adjuvant therapy in breast cancer patients, including, but not limited to combinations of 2 cyclophosphamide, doxorubicin, vincristine methotrexate, 5-fluorouracil and/or leucovorin. In a specific embodiment, the present invention provides hsp compositions and methods for enhancing specific immunity to preneoplastic and neoplastic mammary cells in women. The present invention also provides compositions and methods for preventing the development of neoplastic cells in women at enhanced risk for breast cancer, and for inhibiting cancer cell proliferation and metastasis. These compositions can be applied alone or in combination with each other or with biological response modifiers.

5.8. Prevention and Treatment of Primary and Metastatic Neoplastic Diseases

There are many reasons why immunotherapy as provided by the present invention is desired for use in cancer patients. First, if cancer patients are immunosuppressed and surgery, with anesthesia, and subsequent chemotherapy, may worsen the immunosuppression, then with appropriate immunotherapy in the preoperative period, this immunosuppression may be prevented or reversed. This could lead to fewer infectious complications and to accelerated wound healing. Second, tumor bulk is minimal following surgery and immunotherapy is most likely to be effective in this situation. A third reason is the possibility that tumor cells are shed into the circulation at surgery and effective immunotherapy applied at this time can eliminate these cells.

In a specific embodiment, the preventive and therapeutic methods of the invention are directed at enhancing the immunocompetence of the cancer patient either before surgery, at or after surgery, and to induce tumor-specific immunity to cancer cells, with the objective being inhibition of cancer, and with the ultimate clinical objective being total cancer regression and eradication.

5.9. Monitoring of Effects During Cancer Prevention and Immunotherapy with Hsp-peptide Complexes The effect of immunotherapy with hsp-antigenic molecule complexes on development and progression of neoplastic diseases can be monitored by any methods known to one skilled in the art, including but not limited to measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; e) changes in levels of putative biomarkers of risk for a particular cancer in individuals at high risk, and f) changes in the morphology of tumors using a sonogram.

5.9.1. Delayed Hypersensitivity Skin Test

Delayed hypersensitivity skin tests are of great value in the overall immunocompetence and cellular immunity to an antigen. Inability to react to a battery of common skin antigens is termed anergy (Sato, T., et al, 1995, *Clin. Immunol. Pathol.* 74:35–43).

Proper technique of skin testing requires that the antigens be stored sterile at 4° C., protected from light and reconstituted shorted before use. A 25- or 27-gauge need ensures intradermal, rather than subcutaneous, administration of antigen. Twenty-four and 48 hours after intradermal administration of the antigen, the largest dimensions of both erythema and induration are measured with a ruler. Hypoactivity to any given antigen or group of antigens is confirmed by testing with higher concentrations of antigen or, in ambiguous circumstances, by a repeat test with an intermediate test.

5.9.2. Activity of Cytolytic T-lymphocytes In Vitro $8 \times 10^6$ Peripheral blood derived T lymphocytes isolated by the Ficoll-Hypaque centrifigation gradient technique, are restimulated with $4 \times 10^4$ mitomycin C treated tumor cells in 3 ml RPMI medium containing 10% fetal calf serum. In some experiments, 33% secondary mixed lymphocyte culture supernatant or IL-2, is included in the culture medium as a source of T cell growth factors.

In order to measure the primary response of cytolytic T-lymphocytes after immunization, T cells are cultured without the stimulator tumor cells. In other experiments, T cells are restimulated with antigenically distinct cells. After six days, the cultures are tested for cytotoxity in a 4 hour $^{51}$Cr-release assay. The spontaneous $^{51}$Cr-release of the targets should reach a level less than 20%. For the anti-MHC class I blocking activity, a tenfold concentrated supernatant of W6/32 hybridoma is added to the test at a final concentration of 12.5% (Heike M., et al., *J. Immunotherapy* 15:165–174).

5.9.3. Levels of Tumor Specific Antigens

Although it may not be possible to detect unique tumor antigens on all tumors, many tumors display antigens that distinguish them from normal cells. The monoclonal antibody reagents have permitted the isolation and biochemical characterization of the antigens and have been invaluable diagnostically for distinction of transformed from nontransformed cells and for definition of the cell lineage of transformed cells. The best-characterized human tumor-associated antigens are the oncofetal antigens. These antigens are expressed during embryogenesis, but are absent or very difficult to detect in normal adult tissue. The prototype antigen is carcinoembryonic antigen (CEA), a glycoprotein found on fetal gut an human colon cancer cells, but not on normal adult colon cells. Since CEA is shed from colon carcinoma cells and found in the serum, it was originally thought that the presence of this antigen in the serum could be used to screen patients for colon cancer. However, patients with other tumors, such as pancreatic and breast cancer, also have elevated serum levels of CEA. Therefore, monitoring the fall and rise of CEA levels in cancer patients undergoing therapy has proven useful for predicting tumor progression and responses to treatment.

Several other oncofetal antigens have been useful for diagnosing and monitoring human tumors, e.g., alpha-fetoprotein, an alpha-globulin normally secreted by fetal liver and yolk sac cells, is found in the serum of patients with liver and germinal cell tumors and can be used as a matter of disease status.

5.9.4. Computed Tomographic (CT) Scan

CT remains the choice of techniques for the accurate staging of cancers. CT has proved more sensitive and specific than any other imaging techniques for the detection of metastases.

5.9.5. Measurement of Putative Biomarkers

The levels of a putative biomarker for risk of a specific cancer are measured to monitor the effect of hsp noncovalently bound to peptide complexes. For example, in individuals at enhanced risk for prostate cancer, serum prostate-specific antigen (PSA; is measured by the procedure described by Brawer, M. K., et. al., 1992, *J. Urol.* 147:841–845, and Catalona, W. J., et al., 1993, *JAMA* 270:948–958; or in individuals at risk for colorectal cancer CEA is measured as described above in Section 4.5.3; and in individuals at enhanced risk for breast cancer, 16-α-hydroxylation of estradiol is measured by the procedure described by Schneider, J. et al., 1982, *Proc. Natl. Acad. Sci. USA* 79:3047–3051. The references cited above are incorporated by reference herein in their entirety.

5.9.6. Sonogram

A sonogram remains an alternative choice for technique for the accurate staging of cancers.

6. EXAMPLE

Administration of hsp-exogenous Antigens in the Treatment of Hepatocellular Carcinoma Patients with hepatocellular carcinoma are injected with hsp-antigenic molecule peptide complexes prepared in vitro from purified hsp and purified antigen. The antigen used is carcinoembryonic antigen (CEA). Treatment with hsp-antigen complexes is started any time after surgery. However, if the patient has received chemotherapy, hsp-antigen complexes are usually administered after an interval of four weeks or more so as to allow the immune system to recover. The immunocompetence of the patient is tested by procedures described in sections 5.9 above.

The therapeutic regimen includes weekly injections of the hsp-antigen complex, dissolved in saline or other physiologically compatible solution.

The dosage used for hsp70 or gp96 is in the range of 10–600 micrograms, with the preferred dosage being 10–100 micrograms. The dosage used for hsp90 is in the range of 50 to 5,000 micrograms, with the preferred dosage being about 100 micrograms.

The route and site of injection is varied each time, for example, the first injection is given subcutaneously on the left arm, the second injection on the right arm, the third injection on the left abdominal region, the fourth injection on the right abdominal region, the fifth injection on the left thigh, the sixth injection on the right thigh, etc. The same site is repeated after a gap of one or more injections. In addition, injections are split and each half of the dose is administered at a different site on the same day.

Overall, the first four to six injections are given at weekly intervals. Subsequently, two injections are given at two-week intervals, followed by a regimen of injections at monthly intervals. The effect of hsp-antigen complexes therapy is monitored by measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; and e) changes in putative biomarkers of risk for a particular cancer in individuals at high risk.

Depending on the results obtained, the therapeutic regimen is developed to maintain and/or boost the immunological responses of the patient, with the ultimate goal of achieving tumor regression and complete eradication of cancer cells.

7. EXAMPLE

Administration of hsp-exogenous Antigen Complexes in the Treatment of Colorectal Cancer Hsp-antigen complexes (comprising gp96, hsp70, hsp90 or a combination thereof) are administered as adjuvant therapy and as prophylactic adjuvant therapy in patients after complete reduction of colorectal cancer to eliminate undetectable micrometastases and to improve survival.

The therapeutic and prophylactic regimens used in patients suffering from colorectal cancer are the same as those described in Section 6 above for patients recovering with hepatocellular carcinoma. The antigen used as the exogenous antigenic molecule is carcinoembryonic antigen. The methods of monitoring of patients under clinical evaluation for prevention and treatment of colorectal cancer is done by procedures described in Section 5.9.

8. EXAMPLE

Induction of CTL-response to hsp70-ovalbumin Complex

8.1. Materials and Methods

Hsp70-ovalbumin complex was prepared in vitro. Briefly, 5–10 micrograms of purified hsp70 was incubated with equimolar quantities of ovalbumin in 20 mM sodium phosphate buffer pH 7.5, 0.5 NaCl, 3 mM $MgCl_2$ and 1 mM ADP in a volume of 100 microliter at 37° C. for 1 hour. This incubation mixture was then further diluted to 1 ml in phosphate-buffered saline and injected sub-cutaneously into the mammal of choice, the C57BL/6 strain of mice.

The injections were repeated once a week interval. The hsp70-ovalbumin complex was prepared fresh for each injection. A total of two injections was administered before sacrificing the animals. Two mice in each group were immunized with: a) control vehicle; b) ovalbumin alone; c) hsp70 alone; or d) hsp70-ovalbumin complex.

T cells were isolated from the spleen of each mouse using the T cell-gradient centrifugation technique and $8\times10^5$ T cells were incubated with $4\times10^4$ EG7 cells (positive for ovalbumin antigen) or EL4 cells (negative for ovalbumin antigen). The CTL response was measured as $\%^{51}Cr$ release.

8.2. Results

Hsp70-ovalbumin complex induced a far greater CTL response than ovalbumin alone or hsp70 alone (FIG. 1A). However, the T cells did not respond to the EL4 cells which lack the ovalbumin antigen (FIG. 1B).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of eliciting an immune response against an antigenic peptide or protein in an individual comprising administering to the individual a complex of a heat shock protein noncovalently bound to the antigenic peptide or protein, wherein the complex is made in vitro, and wherein the antigenic peptide or protein is not isolated from a heat shock protein-antigenic peptide or protein complex from within a cell.

2. The method according to claim 1 wherein the antigenic peptide or protein is selected from the group consisting of a cancer antigen, an antigen of an infectious agent, and a molecule displaying antigenicity of a cancer antigen or antigen of an infectious agent.

3. The method according to claim 2 wherein the antigenic peptide or protein is a cancer antigen from a cancer selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, and heavy chain disease.

4. The method according to claim 2 wherein the antigenic peptide or protein is an antigen of an infectious agent selected from the group consisting of a virus, bacterium, protozoan, and parasite.

5. The method according to claim 4 wherein the infectious agent is a virus selected from the group consisting of hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, human immunodeficiency virus type I (HIV-I), and human immunodeficiency virus type II (HIV-II).

6. The method according to claim 4 wherein the infectious agent is a bacterium selected from the group consisting of mycobacteria, rickettsia, mycoplasma, neisseria and legionella.

7. The method according to claim 4 wherein the infectious agent is a protozoan selected from the group consisting of leishmania, kokzidioa, and trypanosoma.

8. The method according to claim 4 wherein the infectious agent is a parasite selected from the group consisting of chlamydia and rickettsia.

9. The method according to claim 1 wherein the heat shock protein is selected from the group consisting of hsp70, hsp90, and gp96.

10. The method according to claim 1 wherein the heat shock protein is hsp70.

11. The method according to claim 1 wherein the heat shock protein is hsp90.

12. The method according to claim 1 wherein the heat shock protein is gp96.

13. The method according to claim 1 wherein the individual is a human.

14. The method according to claim 1 wherein the antigenic peptide or protein is a tumor-specific antigen, a tumor-associated antigen, or an antigenic fragment of a tumor-specific antigen or tumor-associated antigen.

15. The method according to claim 1 wherein the complex comprises a population of complexes wherein the heat shock protein is a combination of hsp70 and hsp90, hsp70 and gp96, hsp90 and gp96, or hsp70, hsp90, and gp96.

* * * * *